(12) United States Patent
Halbert et al.

(10) Patent No.: US 8,998,100 B2
(45) Date of Patent: Apr. 7, 2015

(54) INFUSION SYSTEM CONFIGURED FOR TRANSFER OF DATA

(71) Applicant: CareFusion 303, Inc., San Diego, CA (US)

(72) Inventors: Donald Halbert, San Diego, CA (US); Stephen Bollish, San Diego, CA (US); Timothy W. Vanderveen, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 13/927,847

(22) Filed: Jun. 26, 2013

(65) Prior Publication Data

US 2015/0001285 A1    Jan. 1, 2015

(51) Int. Cl.
*G06K 19/00* (2006.01)
*G06F 19/00* (2011.01)

(52) U.S. Cl.
CPC .................................. *G06F 19/323* (2013.01)

(58) Field of Classification Search
USPC ......................... 235/435, 439, 451, 487, 492
See application file for complete search history.

(56) References Cited

U.S. PATENT DOCUMENTS

2011/0241878 A1* 10/2011 Hoag ........................... 340/540

* cited by examiner

*Primary Examiner* — Matthew Mikels
(74) *Attorney, Agent, or Firm* — Fred C. Hernandez; Mintz Levin Cohn Ferris Glovsky and Popeo, P.C.

(57) ABSTRACT

A system and a method are configured to program, track and/or monitor infusion data (such as proper medication, dosage information, drug identification, patient identification, and/or other information believed to be relevant) for a drug infusion system. An electronic data tag, such as a radio frequency identification device ("RFID") tag, may be coupled to one or more components of the infusion system, such as a medication container or infusion set.

11 Claims, 5 Drawing Sheets

INFUSION SYSTEM CONFIGURED FOR TRANSFER OF DATA

BACKGROUND

Physicians and other medical personnel apply intravenous ("IV") infusion therapy to treat various medical conditions in patients. IV infusion therapy typically involves infusing medical fluids, such as medications, IV fluids or IV nutrients, from a fluid supply or container, such as a bag or bottle, through a fluid administration set to a cannula inserted into a patient's blood vessel.

Hospitals and other institutions continually strive to provide quality patient care. Medical errors, such as when a patient receives the wrong medication or receives the correct medication at the wrong time or in the wrong dosage, are significant problems for all health care facilities. The errors may vary and include errors in the administration route and errors in timing of the administration of medication. Despite significant quality control procedures, there still exists some risk that an incorrect fluid container may become mounted to a pump or pump channel.

It is desirable to have a system and method that provide for accurate and efficient communication between a medical fluid container, an infusion pump, and a patient for verifying that the right medication is delivered to the right patient at the right operating parameters. A further need has been recognized for a system and method that automatically updates the patient's medication administration record. The present invention fulfills these needs and others.

SUMMARY

Disclosed is a system and method configured to program, track and/or monitor infusion data (such as proper medication, dosage information, drug identification, patient identification, and/or other information believed to be relevant) for a drug infusion system. An electronic data tag, such as a radio frequency identification device ("RFID") tag, may be coupled to one or more components of the infusion system, such as a medication container or infusion set (sometimes referred to as an infusion cassette.) The electronic data tag may be read and/or written with the infusion data at any of a variety of locations, as described in detail below. The electronic data tags may be used to ensure that the proper medication and dosage are delivered to the patient for whom that medication and dosage are intended.

In one aspect, there is disclosed a method for administering infusion data associated with a drug infusion system, the method comprising: writing infusion data to an electronic tag associated with the infusion system, the data tag being coupled to a first component of the infusion system; positioning the electronic data tag and the first component of the infusion system within a predetermined distance of a second component of the infusion system; and accessing the infusion data via the electronic data tag.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

Disclosed is a system and method configured to program, track and/or monitor infusion data (such as proper medication, dosage information, drug identification, patient identification, and/or other information believed to be relevant) for a drug infusion system. An electronic data tag, such as a radio frequency identification device ("RFID") tag, may be coupled to one or more components of the infusion system, such as a medication container or infusion set (sometimes referred to as an infusion cassette.) The electronic data tag may be read and/or written with the infusion data at any of a variety of locations, as described in detail below. The electronic data tags may be used to ensure that the proper medication and dosage are delivered to the patient for whom that medication and dosage are intended.

Figure 1:
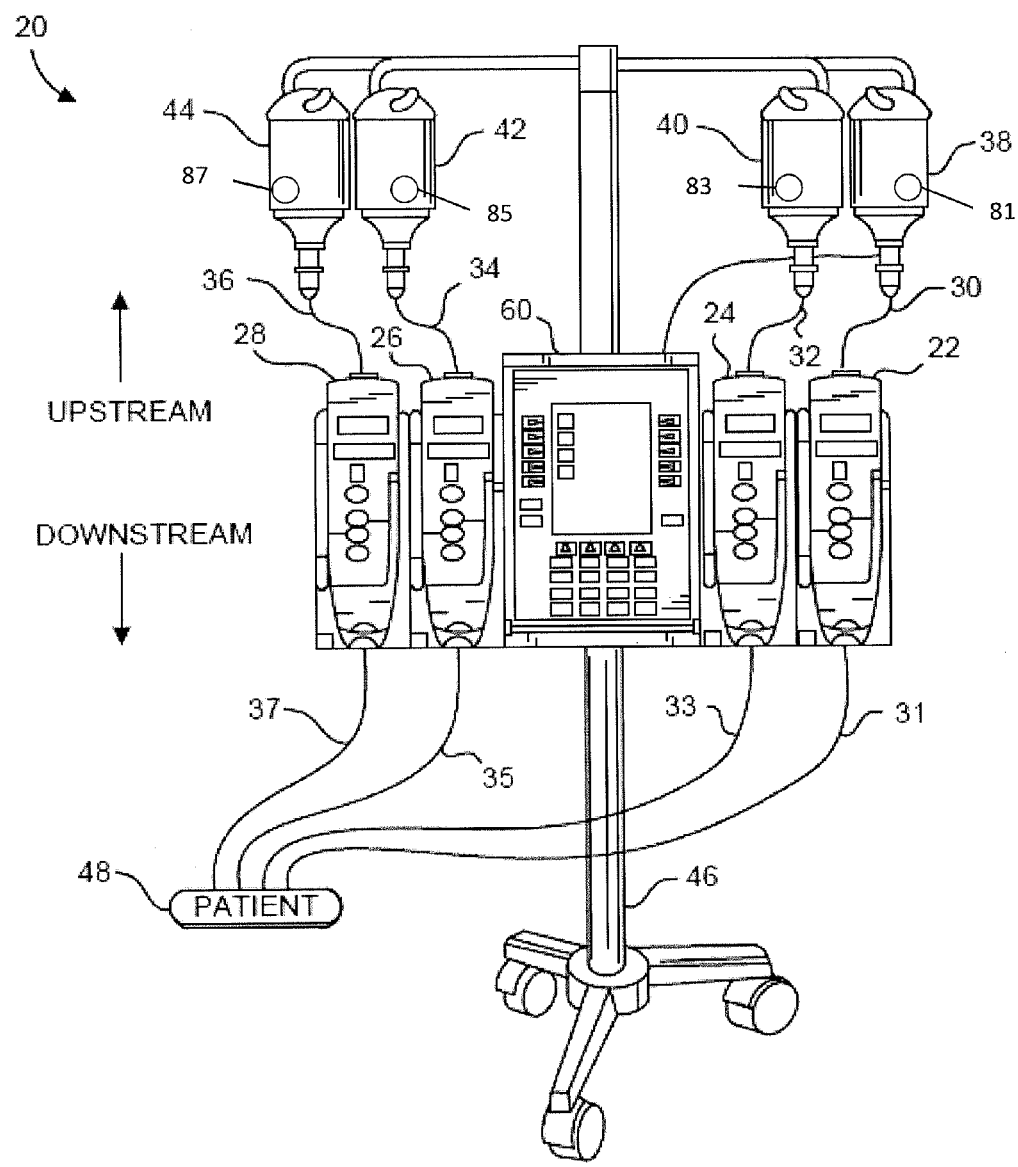
FIG. 1 is a front view of a patient care system having four fluid infusion pumps, each of which is connected to a respective fluid supply for pumping the contents of the fluid supply to a patient.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to a roller stand, IV pole 46, table top, etc.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 1. Many have check valves, drip chambers, valved injection ports, connectors, and other devices well known to those skilled in the art. These other devices have not been included in the drawings so as to preserve clarity of illustration.

It should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater. There would be more of an opportunity for the upstream fluid lines 30, 32, 34, and 36 to become intertwined with each other when all four are dangling from the bottles, which can cause confusion as to which administration set is loaded into which infusion module. The opportunity for confusion increases as the number of administration sets increases.

Figure 2:
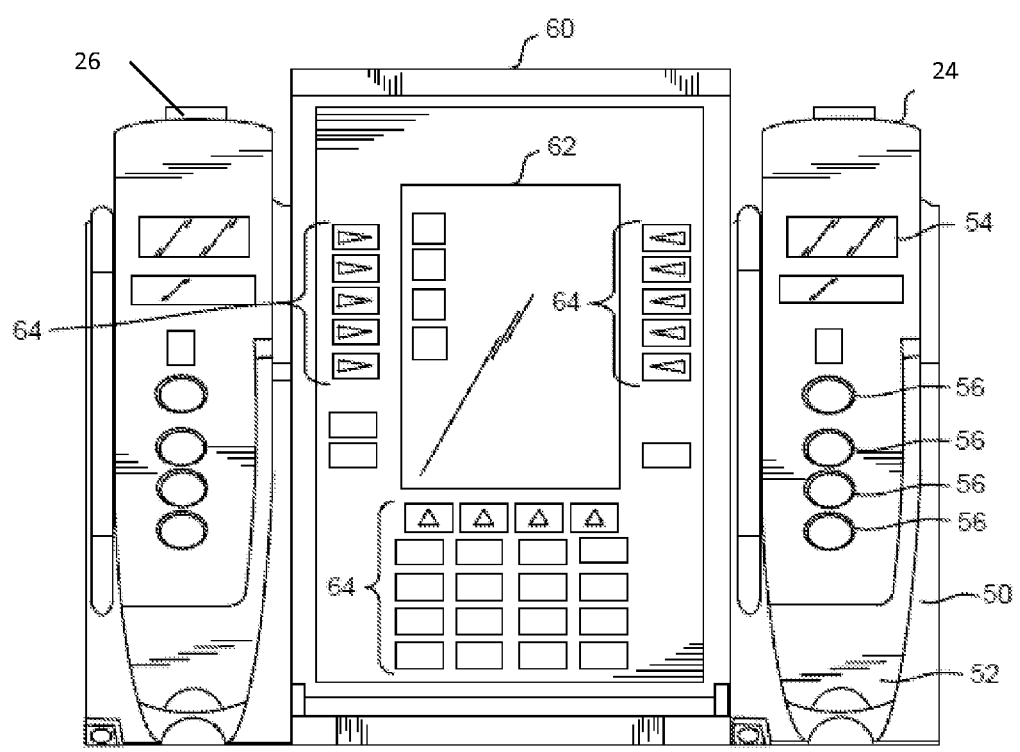
FIG. 2 is an enlarged view of a portion of the patient care system of FIG. 1 showing two of the fluid infusion pumps mounted at either side of a programming module, and the displays and control keys of each, with the programming module being capable of programming both infusion pumps.

Referring now to FIG. 2, an enlarged view of the front of the infusion pump 24 is shown. The pump includes a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 3. When the door is closed, the tube is brought into operating engagement with the pumping mechanism, the upstream and downstream pressure sensors, and the other equipment of the pump. A display 54, such as an LCD or LED display, is located in plain view on the door in this embodiment and may be used to visually communicate various information relevant to the pump, such as alert indications (e.g., alarm messages). Control keys 56 exist for programming and controlling operations of the infusion pump as desired. The infusion pump 24 also includes audio alarm equipment in the form of a speaker (not shown).

In the embodiment shown, a programming module 60 is attached to the left side of the infusion pump 24. Other devices or modules, including another infusion pump, may be attached to the right side of the infusion pump 24, as shown in FIG. 1. In such a system, each attached pump represents a pump channel of the overall patient care system 20. In one embodiment, the programming module is used to provide an interface between the infusion pump 24 and external devices as well as to provide most of the operator interface for the infusion pump 24.

The programming module 60 includes a display 62 for visually communicating various information, such as the operating parameters of the pump 24 and alert indications and alarm messages. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump. This may be done wirelessly or in a wired arrangement such as via a local device.

The communications system may take the form of a radio frequency ("RF") (radio frequency) system, an optical system such as infrared, a Blue Tooth system, or other wired or wireless system. The bar code scanner and communications system may alternatively be included integrally with the infusion pump 24, such as in cases where a programming module is not used, or in addition to one with the programming module. Further, information input devices need not be hardwired to medical instruments, information may be transferred through a wireless connection as well.

FIG. 2 includes a second pump module 26 connected to the programming module 60. As shown in FIG. 1, more pump modules may be connected. Additionally, other types of modules may be connected to the pump modules or to the programming module.

Figure 3:
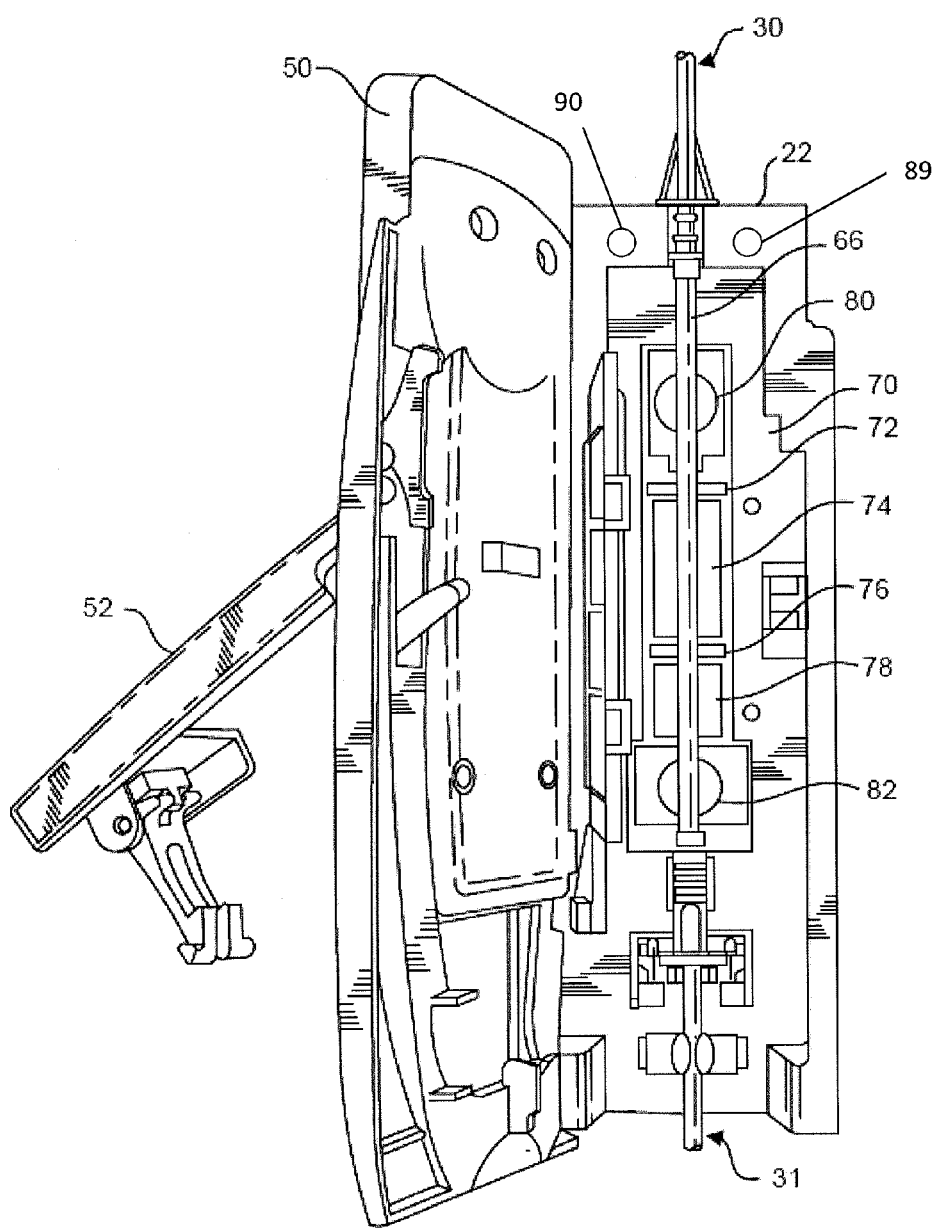
FIG. 3 is a perspective view of one of the fluid infusion pumps of FIGS. 1 and 2 with its front door in the open.

Turning now to FIG. 3, an infusion pump 22 is shown in perspective view with the front door 50 open, showing the upstream fluid line 30 and downstream fluid line 31 in operative engagement with the pump 22. The infusion pump 22 directly acts on a tube 66 that connects the upstream fluid line 30 to the downstream fluid line 31 to form a continuous fluid conduit, extending from the respective fluid supply 38 (FIG. 1) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 2, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 3 further shows a downstream pressure sensor 82 included in the pump 22 embodiment at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 1) and the flow control device, so that the connection of the correct fluid supply with the correct pump may be verified before any fluid is pumped to the patient.

With reference still to FIG. 3, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 1) and the flow control device, so that the connection of the correct fluid supply with the correct pump may be verified before any fluid is pumped to the patient.

Infusion Data System

As mentioned, the infusion system is configured to program, track and/or monitor infusion data (such as proper medication, dosage information, drug identification, patient identification, timing of medication delivery and/or other information believed to be relevant). The data may also include route of administration for the drug or device. An electronic data tag, such as a radio frequency identification device ("RFID") tag, may be coupled to one or more components of the infusion system. The electronic data tag may be read and/or written with the infusion data at any of a variety of locations, as described in detail below. In addition, one or more components of the infusion system may be equipped with an electronic data reader or transmitter for reading and transmitting data to or from the electronic data tag. In an embodiment, electronic data tag is a near field data tag that can be read only when a data reader comes with a predetermined distance of the data tag.

With reference again to FIG. 1, in an embodiment the fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

The pumps or a portion of the pump may also be equipped with an electronic data tag or data transmitter. For example, as shown in FIG. 3, a pump may be equipped with a data tag 89 or a reader device 90 for providing or receiving infusion data. The data reader devices may comprise RFID readers (or receivers) or other wireless devices that are compatible with the data tags associated with the fluid containers. A data transmitter may transmit interrogation signals to the electronic data tags 81, 83, 85, 87 associated with the fluid containers for obtaining infusion data from those tags. Although referred to as data transmitting devices or RFID tags or RFID transponders, data transmitting devices may also receive or read data and may also re writable.

The infusion data associated with the data tags may vary and may include, for example, the patient's name, hospital identification number, and other information such as the patient's age, weight, condition, Body Surface Area (BSA) and allergies. The data may also include, for example, the patient's MAR (medication administration record), a drug identifier, a drug concentration, a diluent fluid identifier, a dose or flow rate, other pumping-related parameters, contra-indicated medications/conditions, bolus dosing rates, Air-In-Line limits and IV occlusion limits for a pump device, and the expiration date of the compounded medication. For example, the data may include information as to when the medication must be administered within relative to an initial compounding in the pharmacy. Contra-indications generally includes information as to whether a drug contraindicated given the patient's condition or diagnosis. Contra-indications may also include information as to patient allergy of a drug, or that a drug is incompatible from a physicochemical standpoint with other drugs the patient is receiving in the same IV line.

Figure 4:
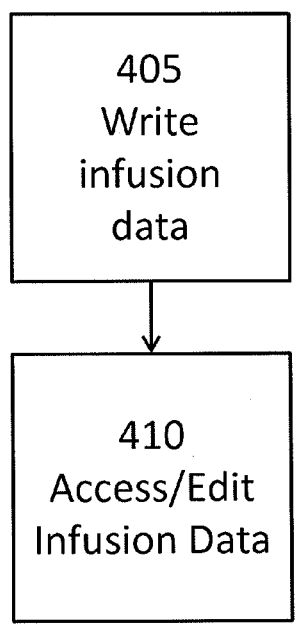
FIG. 4 is a block diagram showing components of one embodiment of the patient care system

FIG. 4 show an exemplary method of using the data tags in connection with the infusion data system. In a first step 405, a user writes infusion data to at least one data tag associated with the infusion system. As mentioned, the contents of the infusion data may vary widely. In an embodiment, a user writes the infusion data to the data tag such that the data tag contains the infusion data itself. For example, the user may write information such as patient name, drug ID, infusion schedule, etc. to the electronic data tag such that all or a portion of the data is stored directly on the tag. This permits a user to access the data by reading it directly from the tag.

In another embodiment, the actual infusion data is not stored on the tag. Rather, an identifier, such as an alphanumeric identifier, is stored on the data tag. The identifier provides a link to a remote location, such as a server, from which the infusion data may be accessed. The remote location may be a central database where infusion data for one or more patients is stored and associated with the identifier. This provides a central location that can be easily managed and reduces the risk that multiple data tags will have conflicting or inconsistent infusion data for a patient. It also provides a means by which the infusion may be securitized by limiting access to read/write capabilities of the central databases and servers.

With reference still to step 405 of FIG. 4, the infusion data (or the patient identifier associated with the infusion data) can be written to the data tag at any of a variety of locations. For example, where the electronic data tag is on the drug container, the infusion data may be written to the data tag at the pharmacy where the drug is initially prepared. If the infusion data is stored directly on the electronic data tag, then the user writes the data directly to the data tag. If the infusion data is stored at a central database, then a link to the central database is accessed to write the data to the central database (assuming that the entity that is writing the data has proper authorization).

The infusion data may also be written and/or revised at locations other than the pharmacy, such as at a hospital location or at any location where the electronic data tag may be accessed. In this regard, any person with proper authorization may write to the electronic data tag. The electronic data tag electronic data tag can serve as a unique identification to access infusion data via a centralized service.

In the next step 410, the user accesses and/or edits infusion data from the electronic data tag. The infusion data may be accessed manually using a data reader. For example, a nurse or other practitioner may couple a data reader to the data tag to read the infusion data. The nurse may then use the infusion data such as to program an infusion pump pursuant to a drug infusion schedule contained in the infusion data.

Or, accessing of the data may occur automatically such as by the electronic data tag coming within a predetermined distance to a device that includes a data reader. For example, one of the infusion pumps may include a data reader that automatically accesses the infusion data from a data tag that comes within a predetermined distance to the infusion pump. The infusion pump may then use the infusion data to automatically populate the infusion data into the infusion pump and to program the infusion pump pursuant to the data.

The electronic data tag may also be used for tracking of drug contained in a container, syringe, etc. The data tag associated with the drug container may be read along with corresponding location data (such as via a GPS). The location data may then be logged in the data tag or at the central database to provide a means of tracking variations in the location of the drug container.

Exemplary Computing Landscape

Figure 5:
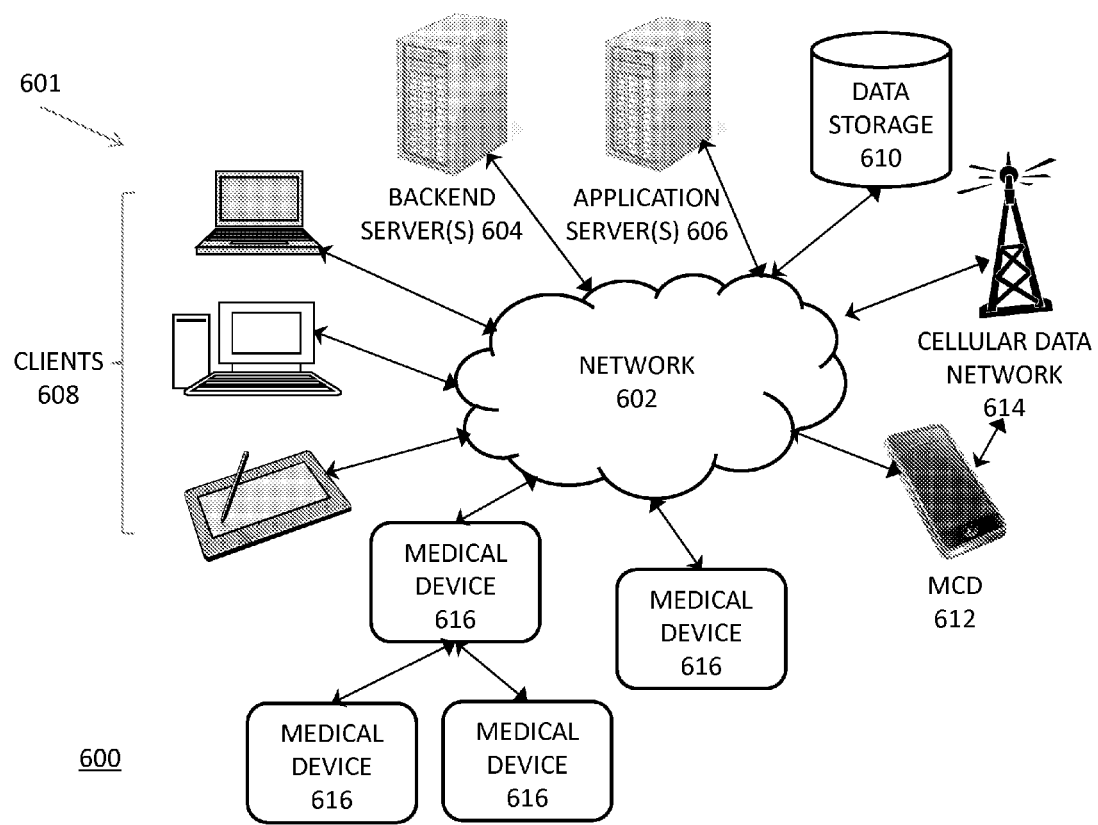
FIG. 5 is a system diagram illustrating a possible computing landscape for an infusion system.

FIG. 5 is a system diagram 600 illustrating a possible computing landscape 601 for the infusion system. The computing landscape 601 can include the infusion system within a healthcare environment, such as a hospital, a clinic, a laboratory, or any other environment. Various devices and systems, both local to the healthcare environment and remote from the healthcare environment, can interact via at least one computing network 602. This computing network 602 can provide any form or medium of digital communication connectivity (that is, wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

In particular, aspects of the computing landscape 601 can be implemented in a computing system that includes a back-end component (for example, as a data server 604), or that includes a middleware component (for example, an application server 606), or that includes a front-end component (for example, a client computer 608 having a graphical user interface or a Web browser through which a user can interact with an implementation of the subject matter described herein), or any combination of such back-end, middleware, or front-end components. A client 608 and servers 604 and 606 are generally remote from each other and typically interact through the communications network 602. The relationship of the clients 608 and servers 604, 606 arises by virtue of computer programs running on the respective computers and having a client-server relationship to each other. Clients 608 can be any of a variety of computing platforms that include local applications for providing various functionalities within the healthcare environment. Example clients 608 include, but are not limited to, desktop computers, laptop computers, tablets, and other computers with touch-screen interfaces. The local applications can be self-contained in that they do not require network connectivity and/or they can interact with one or more of the servers 604, 606 (for example, a web browser).

A variety of applications can be executed on the various devices and systems within the computing landscape such as electronic health record applications, medical device monitoring, operation, and maintenance applications, scheduling applications, billing applications and the like.

The network 602 can be coupled to one or more data storage systems 610. The data storage systems 610 can include databases providing physical data storage within the healthcare environment or within a dedicated facility. In addition, or in the alternative, the data storage systems 610 can include cloud-based systems providing remote storage of data in, for example, a multi-tenant computing environment. The data storage systems 610 can also comprise non-transitory computer readable media.

Mobile communications devices 612 can also form part of the computing landscape 601. The mobile communication devices 612 can communicate directly via the network 602 and/or they can communicate with the network 602 via an intermediate network such as a cellular data network 614. Various types of communication protocols can be used by the mobile communication devices 612 including, for example, messaging protocols such as SMS and MMS.

Various types of medical devices 616 can be used as part of the computing landscape 601. The medical devices 616 can include one or more of the infusion system and associated devices. These medical devices 616 can include, unless otherwise specified, any type of device or system with a communications interface that characterizes one or more physiological measurements of a patient and/or that characterize treatment of a patient. In some cases, the medical devices 616 communicate via peer to peer wired or wireless communications with another medical device 616 (as opposed to communicating with the network 602). For example, the medical device 616 can comprise a bedside vital signs monitor that is connected to other medical devices 616, namely a wired, or wireless pulse oximeter and to a wired blood pressure monitor. One or more operational parameters of the medical devices 616 can be locally controlled by a clinician, controlled via a clinician via the network 602, and/or they can be controlled by one or more of a server 604 and/or 606, a client 608, a mobile communication device 612, and/or another medical device 616.

The computing landscape 601 can provide various types of functionality as can be required within a healthcare environment such as a hospital. For example, a pharmacy can initiate a prescription via one of the client computers 608. This prescription can be stored in the data storage 610 and/or pushed out to other clients 608, a mobile communication device 612, and/or one or more of the medical devices 616. In addition, the medical devices 616 can provide data characterizing one or more physiological measurements of a patient and/or treatment of a patient (for example, medical device 616 can be an infusion management system, etc.). The data generated by the medical devices 616 can be communicated to other medical devices 616, the servers 604 and 606, the clients 608, the mobile communication devices 612, and/or stored in the data storage systems 610.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above.

In addition, the logic flow(s) when depicted in the accompanying figures and/or described herein do not necessarily require the particular order shown, or sequential order, to achieve desirable results. Other implementations may be within the scope of the following claims.

The invention claimed is:

1. A method for managing infusion data associated with a drug infusion system, the method comprising:
   electronically accessing an identifier on an electronic data tag coupled to a first component of the infusion system, wherein the identifier provides a link to a remote location from which infusion data associated with a patient may be accessed;
   positioning the electronic data tag and the first component of the infusion system within a predetermined distance of a second component of the infusion system; and
   accessing the infusion data via the electronic data tag by downloading the infusion data from the remote location.

2. A method as in claim 1, wherein the identifier is accessed automatically upon the electronic data tag and the first component of the infusion system moving within a predetermined distance of the second component of the infusion system.

3. A method as in claim 1, wherein accessing the identifier comprises transmitting a radio frequency signal.

4. A method as in claim 1, wherein the infusion data includes at least one of the patient's name, hospital identification number, patient's age, weight, Body Surface Area (BSA), condition, and allergies.

5. A method as in claim 1, wherein the infusion data includes at least one of the patient's medication administration record, a drug identifier, a drug concentration, a diluent fluid identifier, a drug dose or fluid flow rate, and contraindicated medications.

6. A method as in claim 1, wherein the electronic data tag is a radio frequency identification device ("RFID") tag.

7. A method as in claim 1, wherein the first component of the infusion system is a drug container.

8. A method as in claim 1, wherein the second component of the infusion system is an infusion pump.

9. A method as in claim 1, wherein the infusion data includes expiration date of a drug.

10. A method as in claim 1, wherein the infusion data includes at least one of a bolus dosing rate, an air-in-line limit and an IV occlusion limits.

11. A method as in claim 1, further comprising revising the infusion data while located at a patient bedside location.

* * * * *